United States Patent [19]

Stocker

[11] Patent Number: 4,560,647

[45] Date of Patent: Dec. 24, 1985

[54] ANTIBODY/ANTIGEN DETERMINATION METHOD

[75] Inventor: John Stocker, Flüh, Switzerland

[73] Assignee: Hoffmann-La Roche Inc., Nutley, N.J.

[21] Appl. No.: 575,237

[22] Filed: Jan. 30, 1984

Related U.S. Application Data

[63] Continuation of Ser. No. 346,664, Feb. 8, 1982, abandoned.

[30] Foreign Application Priority Data

Feb. 19, 1981 [CH] Switzerland ............... 1104/81
Nov. 27, 1981 [CH] Switzerland ............... 7613/81

[51] Int. Cl.$^4$ ............................................. G01N 33/54
[52] U.S. Cl. ........................................ 435/5; 356/246; 422/72; 436/519; 436/520; 436/534; 436/541; 436/807; 436/828
[58] Field of Search .................. 422/72; 436/520, 828, 436/519, 534, 541, 807; 435/5

[56] References Cited

U.S. PATENT DOCUMENTS

| | | | |
|---|---|---|---|
| 4,021,534 | 5/1977 | Lafontaine | 436/530 |
| 4,048,298 | 9/1977 | Niswender | 436/530 X |
| 4,130,634 | 12/1978 | Molinaro | 422/57 X |
| 4,148,607 | 4/1979 | Bernoco | 422/72 X |
| 4,154,795 | 5/1979 | Thorne | 422/99 |
| 4,169,138 | 9/1979 | Jonsson | 422/57 X |
| 4,273,756 | 6/1981 | Ling | 436/513 X |
| 4,297,104 | 10/1981 | Matte | 422/72 X |

*Primary Examiner*—Sidney Marantz
*Attorney, Agent, or Firm*—Jon S. Saxe; George M. Gould; John J. Maitner

[57] ABSTRACT

A method for the determination of antigens or antibodies in a fluid by incubation of particles, which have antigens on the surface, and antibodies, whereby either the antigens or the antibodies are of known specificity is described. This method comprises introducing the antigen/antibody complex into a container having a conical-shaped or keel-shaped bottom recess, whereby at least the recess of the container is coated with an immunoglobulin-building component which is directed against the antibodies. After centrifugation the amount of the sediment is determined, which indicates whether the antigen or antibody to be determined is present or not.

14 Claims, No Drawings

ANTIBODY/ANTIGEN DETERMINATION METHOD

This is a continuation of application Ser. No. 346,664, filed Feb. 8, 1982, now abandoned.

BACKGROUND OF THE INVENTION

The binding of antibodies to target antigens, which are bound to cells, is a fundamental reaction in all fields of serology and especially of clinical diagnostics. Such binding can be determined by various methods. These methods include the observation of the cell agglutination by the antibodies, the cytotoxicity test, as well as a variety of methods in which there are used labelled antibodies, the presence of which on the cell surface is ascertained by other methods, for example, by radioactivity measurement, by determination of the enzyme substrate reaction as well as by fluorescence measurement. In German Offenlegungsschrift No. 2907198 there is described a sensitive method for the detection of the binding of antibodies to erythrocytes (RBC), which is based on the adherence of the antibody-loaded RBC to a plastic surface. According to this method, the target antigen (A), which is carried by the RBC, reacts with a specific antibody of serum or cells of an animal species X (X-anti-A). After a washing operation, in which excess X-anti-A is removed, there is added a further anti-serum (B) which has a specificity against the determinants of the immunoglobulins of X-anti-A. After a further washing step, the cells are centrifuged in a cuvette, the V-shaped body of which is loaded with immunoglobulin (Ig) of the animal species X(IgX). The cell-bound antibodies (B) have free binding positions, which bind with the IgX, from which there results an adherence of the cells to the plastic material. In the case of a negative reaction, where no anti-A is bound to the cell surface, anti-serum B likewise does not bind, and no adherence of the cells results during the centrifugation. The method described in the aforementioned DOS has two disadvantages, namely:

(a) the requirement of the repeated cell washing steps, which are time-consuming, and (b) the dependence on a defined, critical concentration of X-anti-A on the cell surface, to the extent that just the same as before anti-X binding positions of the cell-bound antiserum (B) are present for the binding of IgX to the plastic surface.

In accordance with the present invention an immunoglobulin-binding component is bound directly to the plastic material of the cuvette and can thus be used in the adherence test for the detection of X-anti-A, which are bound to the cells. In this manner washing steps are eliminated, and the sensitivity of the test is increased.

SUMMARY OF THE INVENTION

The inventions relates to a method for the determination of antigens or antibodies in a fluid by incubation of particles, which have antigens on the surface, and antibodies, whereby either the antigens or the antibodies are of known specificity. The characteristic feature for the method of this invention is that the antigen/antibody complex is introduced into a container having a conical-shaped or keel-shaped bottom recess, whereby at least the recess of the container is coated with immunoglobulin-binding component which is directed against the antibodies. After centrifugation the amount of the sediment is determined, which indicates whether the antigen or antibody to be determined is present or not. The antigen/antibody complex is freed from unbound immunoglobulins before and/or after the introduction into the container. This method is particularly suitable for determining blood group antigens.

DETAILED DESCRIPTION OF THE INVENTION

The invention is directed to a method for the determination of antigens or antibodies in a fluid by incubation of particles, which have antigens on the surface, and antibodies, whereby either the antigens or the antibodies are of known specificity. The method comprises introducing the antigen/antibody complex into a container having a conical-shaped or keel-shaped bottom recess, whereby at least the recess of the container is coated with an immunoglobulin-binding component which is directed against the antibodies, and by determining the amount of the sediment after centrifugation. The antigen/antibody complex is freed from unbound immunoglobulins before and/or after the introduction into the container.

Immunoglobulin-binding components which are useful in the method of this invention include anti-immunoglobulins or protein A (isolated from *Staphylococcus aureus*), whereby, however, it is to be noted that protein A, as is known, only binds immunoglobulin G.

The method of this invention is especially suitable for the determination of viral, cellular or erythrocytic antigens or antiviral, anticellular or antierythrocytic antibodies.

Examples of viral antigens which can be determined by the method of the invention include antigens of hepatitis B, influenza, rabies, rubella and the like. Cellular antigens which can be determined by this method include antigens of the HLA series as well as tumor antigens. The erythrocytic antigens which can be determined by the method of this invention are blood group antigens, rhesus antigens, Kell antigens, MNS antigens, Lewis antigens as well as Duffy antigens.

Antibodies which can be determined according to the method of this invention include those which are formed in the body in response to the antigens mentioned earlier.

The fluid in which the antigens or antibodies are detected can be a biological fluid such as blood, serum, plasma, urine, cerebrospinal liquor, lymph fluid or saliva. In addition, the fluid in which the antigens or antibodies are detected can also be a buffered salt solution, for example, phosphate-buffered sodium chloride solution, as well as fluids having a low ion strength, for example, an aqueous solution containing 0.24 M/l of glycine, 0.003 M/l of $Na_2HPO_4.12H_2O$, 0.003 M/l of $NaH_2PO_4.2H_2O$, 0.03 M/l of NaCl and 0.1 g/l of $NaN_3$.

Examples of a container having a conical-shaped or keel-shaped bottom recess in which the determination of antigens or antibodies is carried out include a cuvette or the well of a microtitre plate.

Insofar as anti-immunoglobulins are used as the immunoglobulin-binding component, it is not strictly necessary to use them in purified form, but it is of advantage to use them in purified form. Affinity chromtography is especially suitable as the purification method for this.

According to a particular aspect of the present invention, the conical-shaped or keel-shaped bottom recesses of the container need not be coated with the immunoglobulin-binding component immediately before the test. Rather, it is possible to coat these conical-shaped or keel-shaped recesses of the container with the immunoglobulin-binding component, to wash-out with water and to air-dry, whereupon the resulting coated container can be stored in a refrigerator at 4° C. until use.

As the immunoglobulin-binding components there can be used, as mentioned above, protein A, which binds to immunoglobulin G, or anti-immunoglobulins.

As the anti-immunoglobulins there can be used those which are directed against the immunoglobulin subclasses of the antibodies. It is, however, also possible to use as the anti-immunoglobulins those which are directed against the light chains of the antibodies and thus offer wider applicability, since they are directed against all immunoglobulin classes. The coating of the conical-shaped or keel-shaped bottom recesses of the container with the anti-immunoglobulins is carried out by methods well known in the art.

As mentioned earlier, the antigen/antibody complex is freed from unbound immunoglobulins before and/or after the introduction into the container. Where this step is undertaken before introduction into the container, it is carried out in the customary manner, i.e., by treatment with a buffer such as phosphate-buffered sodium chloride solution, centrifugation and decantation. This operation may be repeated several times. If this step is undertaken only after the introduction into the container, then it is carried out by centrifuging the fluid containing the antigen/antibody complex through a cushion consisting of a further fluid, the density of the fluid of the cushion being greater than the density of the other fluid. Of course, the cushion fluid must be non-toxic and must have a suitable pH (e.g. in the range of 6–8). Furthermore, this cushion fluid must bring about no change with respect to the succession of layers.

Examples of cushion fluids which can be used are bovine serum albumin, foetal calf serum as well as polyvinylpyrrolidone.

In the case of the determination of serum with low titres, it is recommended to use a preceding washing step as well as the cushion purification method.

As mentioned earlier, after the centrifugation the amount of sediment is determined, this being preferably carried out by measuring its proportional sediment surface.

As particles which have antigens on the surface, there come into consideration especially erythrocytes.

The antigen/antibody determination method of the present invention can be carried out not only manually but also using various devices, for example with the apparatus described in German Offenlegungsschrift No. 2907823.

The following Example illustrates the present invention:

EXAMPLE I

Rhesus determination

1. Preparation of rabbit-anti-human IgG (R-anti-HIgG).

(a) Rabbits are immunized by a first subcutaneous injection of 0.5 mg of human IgG in Freund's complete adjuvant, followed by a second injection, four weeks later, of 0.5 mg of IgG in Freund's incomplete adjuvant. Ten days after the second injection the sera are investigated for antibodies against human IgG with the aid of the Ouchterlony immundiffusion test. Blood is removed from rabbits with high titres of antibodies and the sera are separated and inactivated by heating to 56° C. for 30 minutes.

(b) The specific antibodies against human IgG are purified by affinity chromatography on a human-IgG-Sepharose column. The antiserum is placed on the column, which is then rinsed with phosphate-buffered sodium chloride solution of pH 7.2. The specific antibodies are then eluted from the column with glycine-sodium chloride buffer of pH 2.8. The eluate (R-anti-HIgG) is then dialyzed against phosphate-buffered sodium chloride solution.

2. Coating with R-anti-HIgG or with protein A.

(a) The R-anti-HIgG or the protein A (Pharmacia) is diluted to 10 μg/ml in phosphate-buffered sodium chloride solution. 50 μl are added to each well of a microtitre plate having a V-shaped bottom (Dynatech Laboratories Cat. No. 1-330-25, Virginia, U.S.A.). The plates are incubated at 37° C. for one hour.

(b) The fluid with phosphate-buffered sodium chloride solution and unbound R-anti-HIgG or protein A is removed and the microtitre plates are washed twice with phosphate-buffered sodium chloride solution and then washed briefly with distilled water.

(c) The distilled water is removed immediately, and the microtitre plates are air-dried in a cool stream of air. The dried plates can then be stored at 4° C. until used.

3. Determination of RBC antigens using plates coated with R-anti-HIgG or with protein A.

(a) 100 μl of citrate-anticoagulated donor blood are diluted by adding 5 ml of a buffer having a low ion strength. As the buffer having a low ionic strength there is used glucose in water with 5 mM of HEPES (N-2-hydroxyethyl-piperazine-N'-2-ethanesulphonic acid) buffer.

(b) 50 μl of the diluted blood are incubated at room temperature for 10 minutes with 10 μl of rhesus blood groups-antiserum (Merz and Dade, Düdingen, Switzerland).

(c) 150 μl of 20% bovine serum albumin in phosphate-buffered sodium chloride solution are added to each well of the microtitre plate which is coated with R-anti-HIgG or with protein A.

(d) 25 μl of the incubation mixture from 3 (b) are poured over the surface of the phosphate-buffered sodium chloride solution.

(e) The plates are centrifuged for 5 minutes at 3000 rpm in a centrifuge having a rotation radius of 11 cm (this corresponds to approximately 1100×g).

(f) The extent of the erythrocyte sediment is estimated visually. Where less than 10% of the erythrocytes are present in the sediment the reaction is interpreted as being positive (+), which means that the erythrocytes carry the antigen which is recognized by the antiserum used. Where at least 70% of the erythrocytes are present in the sediment the test is considered to be negative (−). No intermediate results were observed when using rhesus antisera.

4. Results (a) The rhesus determination in accordance with the solid phase antiglobulin method (SPA) provided by the present invention is compared with the customary Coombs antiglobulin method (CT). The results are given in the following Table I.

TABLE I

| Specificity of the rhesus-typical serum | Donor No. 1 | | | Donor No. 2 | | | Donor No. 3 | |
| --- | --- | --- | --- | --- | --- | --- | --- | --- |
| | | SPA | | | SPA | | | SPA |
| | CT | R—anti-HIgG | Protein A | CT | R—anti-HIgG | Protein A | CT | R—anti-HgG |
| C | − | − | − | − | − | − | + | + |
| c | + | + | + | + | + | + | + | + |
| E | + | + | + | − | − | − | − | − |
| e | + | + | + | + | + | + | + | + |
| D | + | + | + | − | − | − | + | + |
| Negative Control (phosphate-buffered sodium chloride solution) | − | − | − | − | − | − | − | − |

I claim:

1. A method for determining in a fluid either (1) antigens associated with particles or (2) antibodies, said method consisting essentially of:
   (a) adding to said fluid either antibodies specific to (1) or antigen, associated with particles, specific to (2), respectively,
   (b) incubating the mixture resulting from (a) so as to permit the formation of an antigen/antibody complex,
   (c) introducing the incubated mixture resulting from (b) into a container having a conical- or keel-shaped bottom recess, wherein at least the recess of the container is coated with an immunoglobulin-binding component directed against the antibodies in the antigen/antibody complex,
   (d) freeing said antigen/antibody complex from unbound immunoglobulins before and/or after introducing the mixture resulting from (b) into said container,
   (e) centrifuging said container,
   (f) determining the amount of sediment in the container after step (e); and
   (g) relating the amount of antigens or antibodies in the original fluid to the amount of sediment determined in step (f).

2. A method according to claim 1, wherein the immunoglobulin-binding component is an anti-immunoglobulin.

3. A method according to claim 1, wherein the immunoglobulin-binding component is protein A.

4. A method according to claim 1, wherein the antigens to be determined are viral, cellular or erythrocytic antigens.

5. A method according to claim 1, wherein the antibodies to be determined are antiviral, anticellular or antierythrocytic antibodies.

6. A method according to claim 1, wherein the fluid is a biological fluid.

7. A method according to claim 1, wherein the fluid is buffered salt solution.

8. A method according to claim 1, wherein the fluid is a buffer having a low ionic strength.

9. A method according to claim 1, wherein the container having a conical-shaped or keel-shaped bottom recess is a cuvette or the well of a microtitre plate.

10. A method according to claim 1, wherein the immunoglobulin-binding component is used in purified form.

11. A method according to claim 2 or claim 10, wherein the anti-immunoglobulins are purified by affinity chromatography.

12. A method according to claim 1, wherein the conical-shaped or keel-shaped bottom recesses of the container are coated with the immunoglobulin-binding component, washed out with water and air-dried.

13. A method according to claim 2, wherein the anti-immunoglobulins are directed against immunoglobulin sub-classes of the antibodies.

14. A method according to claim 2, wherein the anti-immunoglobulins are directed against the light chains of the antibodies.

* * * * *